United States Patent
Mulroney et al.

(10) Patent No.: US 12,195,794 B2
(45) Date of Patent: Jan. 14, 2025

(54) METHODS OF ANALYZING CAPPED RIBONUCLEIC ACIDS

(71) Applicant: The Regents of the University of California, Oakland, CA (US)

(72) Inventors: Logan Mulroney, Santa Cruz, CA (US); Mark Akeson, Santa Cruz, CA (US); Miten Jain, Santa Cruz, CA (US); Hugh Olsen, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1034 days.

(21) Appl. No.: 17/056,378

(22) PCT Filed: May 22, 2019

(86) PCT No.: PCT/US2019/033600
§ 371 (c)(1),
(2) Date: Nov. 17, 2020

(87) PCT Pub. No.: WO2019/226822
PCT Pub. Date: Nov. 28, 2019

(65) Prior Publication Data
US 2021/0348224 A1    Nov. 11, 2021

Related U.S. Application Data

(60) Provisional application No. 62/675,640, filed on May 23, 2018.

(51) Int. Cl.
*C12Q 1/6869* (2018.01)
*C12P 19/34* (2006.01)

(52) U.S. Cl.
CPC ............ *C12Q 1/6869* (2013.01); *C12P 19/34* (2013.01)

(58) Field of Classification Search
CPC . C12Q 1/6869; C12Q 2565/631; C12P 19/34; G01N 33/48721; G01N 33/5308; C12Y 605/01003
See application file for complete search history.

(56) References Cited

U.S. PATENT DOCUMENTS

| | | | |
|---|---|---|---|
| 6,267,872 B1 * | 7/2001 | Akeson | C12Q 1/6869 977/932 |
| 6,746,594 B2 * | 6/2004 | Akeson | C12Q 1/6869 422/50 |
| 11,913,905 B2 * | 2/2024 | Gundlach | B82Y 15/00 |
| 2006/0063196 A1 * | 3/2006 | Akeson | G01N 33/48721 435/7.1 |
| 2008/0045418 A1 * | 2/2008 | Xia | C12Q 1/6806 506/9 |
| 2013/0244340 A1 | 9/2013 | Davis et al. | |
| 2014/0134618 A1 * | 5/2014 | Kokoris | G01N 33/54373 435/6.11 |
| 2014/0284270 A1 * | 9/2014 | Fox | B01D 69/144 210/500.28 |
| 2017/0235877 A1 | 8/2017 | Lo et al. | |
| 2017/0253923 A1 | 9/2017 | Garalde et al. | |

FOREIGN PATENT DOCUMENTS

WO    WO-2016059436 A1 *    4/2016    ............... C12N 9/14

OTHER PUBLICATIONS

Li et al, Nature Methods, vol. 14, pp. 23-31 plus Erratum, published online Dec. 29, 2016.*
Liu et al, J. Genet, Genom., vol. 41, pp. 21-33, published online Nov. 9, 2013.*
Mulroney et al Identification of high-confidence human poly(A) RNA isoform scaffolds using nanopore sequencing (post art), RNA, 2022, vol. 28 No. 2, pp. 162-176. (Year: 2022).*

* cited by examiner

*Primary Examiner* — Narayan K Bhat
(74) *Attorney, Agent, or Firm* — Brian E. Davy; Bozicevic, Field & Francis LLP

(57) ABSTRACT

Provided are methods of analyzing capped ribonucleic acids (RNAs). The methods include translocating an adapted RNA through a nanopore of a nanopore device. The adapted RNA includes an RNA region, a 5' cap, and an adapter polynucleotide attached to the 5' cap. The methods include monitoring ionic current through the nanopore during the translocating, translocating the 5' cap through the nanopore, and identifying one or more ionic current features characteristic of the 5' cap (e.g., a triphosphate linkage between the 5' cap and nucleotide N1 of the RNA region, a 5' to 5' orientation of the 5' cap and nucleotide N1 of the RNA region, and/or the like), translocating through the nanopore. Also provided are computer-readable media, computer devices, and systems that find use, e.g., in practicing the methods of the present disclosure.

25 Claims, 8 Drawing Sheets

Specification includes a Sequence Listing.

Proportion of total nanopore
reads that contain TSS

☒ tss (predicted full length)    ☒ no tss (predicted to be truncated)

Proportion of adapted nanopore
reads that contain TSS

☒ tss (predicted full length)    ☒ no tss (predicted to be truncated)

```
                          SEQUENCE LISTING

<160> NUMBER OF SEQ ID NOS: 2

<210> SEQ ID NO 1
<211> LENGTH: 30
<212> TYPE: DNA
<213> ORGANISM: Artificial sequence
<220> FEATURE:
<223> OTHER INFORMATION: synthetic sequence

<400> SEQUENCE: 1
ggtggtggcg gctctggcgc aggcggggcg                                         30

<210> SEQ ID NO 2
<211> LENGTH: 100
<212> TYPE: DNA
<213> ORGANISM: Artificial sequence
<220> FEATURE:
<223> OTHER INFORMATION: synthetic sequence

<400> SEQUENCE: 2
acactctttc cctacacgac gctcttccga tctggggaga ccaaagcttg gtaccgagct        60
cggatccagc caccatggga gtcaaagttc tgtttgccct                             100
```

METHODS OF ANALYZING CAPPED RIBONUCLEIC ACIDS

CROSS-REFERENCE TO RELATED APPLICATIONS

This application claims the benefit of U.S. Provisional Patent Application No. 62/675,640, filed May 23, 2018, which application is incorporated herein by reference in its entirety.

INTRODUCTION

Recent advances in DNA sequencing have revolutionized the field of genomics, making it possible for even single research groups to generate large amounts of sequence data very rapidly and at a substantially lower cost. These high-throughput sequencing technologies make deep transcriptome sequencing and transcript quantification, whole genome sequencing and resequencing available to many more researchers and projects.

A variety of commercial high-throughput sequencing platforms exist and are described, e.g., in Metzker, M. L. (2010) *Nat. Rev. Genet.* 11:31-46, Morey et al. (2013) *Mol. Genet. Metab.* 110: 3-24, Reuter et al. (2015) *Molecular Cell* 58(4):586-597, and elsewhere. In the Illumina platform, the sequencing process involves clonal amplification of adaptor-ligated DNA fragments on the surface of a glass slide. Bases are read using a cyclic reversible termination strategy, which sequences the template strand one nucleotide at a time through progressive rounds of base incorporation, washing, imaging, and cleavage. In this strategy, fluorescently labeled 3'-O-azidomethyl-dNTPs are used to pause the polymerization reaction, enabling removal of unincorporated bases and fluorescent imaging to determine the added nucleotide. Following scanning of the flow cell with a coupled-charge device (CCD) camera, the fluorescent moiety and the 3' block are removed, and the process is repeated.

An emerging single-molecule strategy that has made significant progress in recent years is nanopore-based sequencing. When a potential is applied across a nanopore, there is a change in the current flow when an analyte, such as a nucleotide, resides transiently in the nanopore for a certain period of time. Nanopore detection of the nucleotide results in a current change of known signature and duration. In the strand sequencing method, a single polynucleotide strand is passed through the pore and the identities of the nucleotides are derived.

Nanopore-based strand sequencing can involve the use of a polynucleotide binding protein adjacent to the nanopore to control the rate of movement of the polynucleotide through the pore. A current limitation of such approaches is that the terminal portion of the polynucleotide passes through the pore without the polynucleotide being bound by the polynucleotide binding protein, such that the terminal portion passes through the pore too quickly for the identities of nucleotides in the terminal region to be determined.

Eukaryotic mRNAs contain a cap structure—an N7-methylated guanosine (or 7-methylguanosine)—linked to the first nucleotide of the RNA via a reverse 5' to 5' triphosphate linkage. The cap has an essential role of cap-dependent initiation of protein synthesis. The cap also functions as a unique identifier for recruiting protein factors for pre-mRNA splicing, polyadenylation and nuclear export, and as a protective group from 5' to 3' exonuclease cleavage. The cap further acts as the anchor for the recruitment of factors that initiate protein synthesis and the 5' to 3' looping of mRNA during translation. Recent studies have revealed that 2'-O methylation of RNA nucleotide N1 is central to the non-self discrimination of innate immune response against foreign RNA.

Capping is the first modification made to RNA polymerase Il-transcribed RNA and takes place co-transcriptionally in the nucleus as soon as the first 25-30 nucleotides are incorporated into the nascent transcript. Three enzymatic activities are required, namely, RNA triphosphatase (TPase), RNA guanylyltransferase (GTase) and guanine-N7 methyltransferase (guanine-N7 MTase). Each of these enzyme activities carries out an essential step in the conversion of the 5' triphosphate of nascent RNA to the cap 0 structure (FIG. 2, top structure). RNA TPase removes the γ-phosphate from the 5' triphosphate to generate 5' diphosphate RNA. GTase transfers a GMP group from GTP to the 5' diphosphate via a lysine-GMP covalent intermediate. The guanine-N7 MTase then adds a methyl group to the N7 amine of the guanine cap to form the cap 0 structure.

SUMMARY

Provided are methods of analyzing capped ribonucleic acids (RNAs). The methods include translocating an adapted RNA through a nanopore of a nanopore device. The adapted RNA includes an RNA region, a 5' cap, and an adapter polynucleotide attached to the 5' cap. The methods include monitoring ionic current through the nanopore during the translocating, translocating the 5' cap through the nanopore, and identifying one or more ionic current features characteristic of the 5' cap (e.g., a triphosphate linkage between the 5' cap and nucleotide N1 of the RNA region, a 5' to 5' orientation of the 5' cap and nucleotide N1 of the RNA region, and/or the like), translocating through the nanopore. Also provided are computer-readable media, computer devices, and systems that find use, e.g., in practicing the methods of the present disclosure.

DETAILED DESCRIPTION

Figure 1:
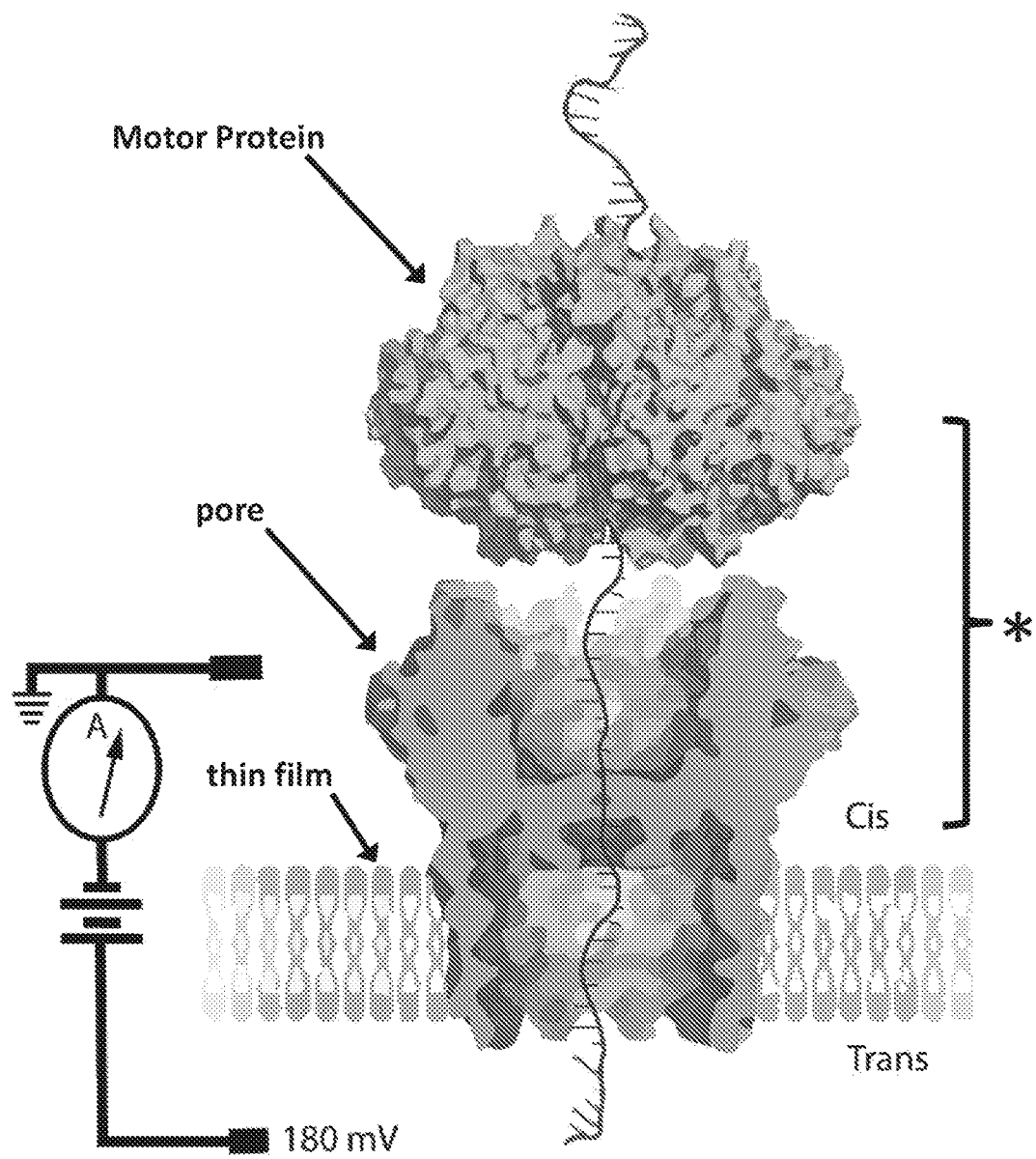
FIG. 1 Schematic illustration of a nanopore and adjacent motor protein. In this example, the motor protein is adjacent to the pore (e.g., a CsgG pore) inserted into a thin film. The distance between the RNA-binding region of the motor protein and the detection region of the nanopore is indicated with an asterisk.

Provided are methods of analyzing capped ribonucleic acids (RNAs). The methods include translocating an adapted RNA through a nanopore of a nanopore device. The adapted RNA includes an RNA region, a 5' cap, and an adapter polynucleotide attached to the 5' cap. The methods include monitoring ionic current through the nanopore during the translocating, translocating the 5' cap through the nanopore, and identifying one or more ionic current features characteristic of the 5' cap (e.g., a triphosphate linkage between the 5' cap and nucleotide N1 of the RNA region, a 5' to 5' orientation of the 5' cap and nucleotide N1 of the RNA region, and/or the like), translocating through the nanopore. Also provided are computer-readable media, computer devices, and systems that find use, e.g., in practicing the methods of the present disclosure.

Before the methods, computer-readable media, computer devices and systems of the present disclosure are described in greater detail, it is to be understood that the methods, computer-readable media, computer devices and systems are not limited to particular embodiments described, as such may, of course, vary. It is also to be understood that the terminology used herein is for the purpose of describing particular embodiments only, and is not intended to be limiting, since the scope of the methods, computer-readable media, computer devices and systems will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, computer-readable media, computer devices and systems. The upper and lower limits of these smaller ranges may independently be included in the smaller ranges and are also encompassed within the methods, computer-readable media, computer devices and systems, subject to any specifically excluded limit in the stated range. Where the stated range includes one or both of the limits, ranges excluding either or both of those included limits are also included in the methods, computer-readable media, computer devices and systems.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, computer-readable media, computer devices and systems belong. Although any methods, computer-readable media, computer devices and systems similar or equivalent to those described herein can also be used in the practice or testing of the methods, computer-readable media, computer devices and systems, representative illustrative methods, computer-readable media, computer devices and systems are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, computer-readable media, computer devices and systems are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, computer-readable media, computer devices and systems, which are, for clarity, described in the context of separate embodiments, may also be provided in combination in a single embodiment. Conversely, various features of the methods, computer-readable media, computer devices and systems, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, computer-readable media, computer devices and systems and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of analyzing capped ribonucleic acids (RNAs) using a nanopore. The methods include translocating an adapted RNA through a nanopore of a nanopore device, where the nanopore device includes a thin film separating a cis compartment from a trans compartment, the thin film including the nanopore therein. The adapted RNA is translocated in the 3' to 5' direction through the nanopore from the cis compartment to the trans compartment, the adapted RNA includes an RNA region, a 5' cap, and an adapter polynucleotide attached to the 5' cap, and the translocating includes translocating the 5' cap through the nanopore. The methods further include monitoring ionic current through the nanopore during the translocating, where the rate of translocation is controlled to permit discrimination of individual nucleotides of the adapted RNA based on changes in the ionic current. The methods further include identifying one or more ionic current features characteristic of the 5' cap translocating through the nanopore.

The methods of the present disclosure enable the analysis of capped RNAs. For example, identifying one or more ionic current features characteristic of a 5' cap translocating through the nanopore provides confirmation that the biological 5' end of the RNA was translocated through the nanopore, as opposed to a fragmented/degraded RNA molecule having a non-biological 5' end. By "biological 5' end" is meant the 5' end of the RNA as originally transcribed and reflecting any splicing of the primary transcript in the cell in which the RNA was produced. Determining the biological 5' ends of RNAs finds use in understanding the 5' untranslated region (UTR), promotor positions, regulatory motifs, the true coding region, and identifying isoforms of alternatively spliced transcripts. Such information is desirable for research, clinical diagnostic, environmental, and other purposes.

The subject methods overcome a limitation of nanopore-based direct RNA analysis (e.g., direct RNA sequencing)—namely, that the 5' terminal portion of the RNA passes through the pore at an uncontrolled rate, such that it is not possible to determine the identities of nucleotides in the 5' terminal portion of the RNA. For example, when a motor protein (e.g., a helicase, polymerase, or the like) is employed to control the rate of 3' to 5' translocation of the RNA through the nanopore, the 5' terminal portion of the RNA passes through the detection region of the nanopore without the RNA being bound by the motor protein (i.e., without the motor protein controlling the rate of translocation) because of the distance between the RNA-binding region of the motor protein and the detection region of the nanopore. An example of such a nanopore and adjacent motor protein is schematically illustrated in FIG. 1. In this example, the motor protein is adjacent a pore, and the distance between the RNA-binding region of the motor protein and the detection region of the nanopore is indicated with an asterisk. Once the terminal nucleotide of the RNA (which may be a 5' cap, such as a 7-methylguanosine cap, if present) is released by the motor protein, the remaining nucleotides between the RNA-binding region of the motor protein and the detection region of the nanopore will translocate past the detection region at an excessive rate such that those nucleotides cannot be identified. According to the methods of the present disclosure, the RNA is a 5' capped RNA with an adapter polynucleotide attached to the 5' cap. In embodiments in which a motor protein is employed to control the rate of translocation of the adapted RNA through the nanopore, the length of the adapter polynucleotide is such that the adapter polynucleotide is available for binding by the motor protein when the 5' cap traverses the detection region of the nanopore. That is, the rate of translocation is controlled all of the way through translocation of the 5' cap through the detection region, permitting analysis (e.g., sequencing) of the complete 5' end of the RNA.

As such, during the translocating, the adapted RNA may be part of a complex including an RNA motor protein and the adapted RNA, where the rate of translocation is controlled by the motor protein. According to such embodiments, the motor protein may be complexed with the adapter polynucleotide during translocation of the 5' cap through the nanopore. By "RNA motor protein" is meant a protein that binds to RNA and is capable of processively regulating movement of the RNA through the nanopore such that discrimination of individual nucleotides of the adapted RNA is permitted. Non-limiting examples of motor proteins which may be employed when practicing the subject methods include an RNA helicase, a DNA helicase, and a reverse transcriptase.

The capped RNA may be from any RNA sample of interest. The RNA sample of interest may be isolated from a single cell, a plurality of cells (e.g., cultured cells), a tissue, an organ, or an organism (e.g., bacteria, yeast, or the like). In certain aspects, the RNA sample of interest is isolated from a cell(s), tissue, organ, and/or the like of an animal. In some embodiments, the animal is a mammal (e.g., a mammal from the genus Homo (e.g., a human), a rodent (e.g., a mouse or rat), a dog, a cat, a horse, a cow, or any other mammal of interest). In other aspects, the RNA sample is isolated/obtained from a source other than a mammal, such as bacteria, yeast, insects (e.g., drosophila), amphibians (e.g., frogs (e.g., *Xenopus*)), viruses, plants, or any other non-mammalian nucleic acid sample source.

Approaches, reagents and kits for isolating RNA from sources of interest are known in the art and commercially available. For example, kits for isolating RNA from a source of interest include the RNeasy®, QIAamp®, QIAprep® and QIAquick® nucleic acid isolation/purification kits by Qiagen, Inc. (Germantown, Md); the ChargeSwitch®, Purelink®, GeneCatcher® nucleic acid isolation/purification kits by Life Technologies, Inc. (Carlsbad, CA); the Nucleo-Mag®, NucleoSpin®, and NucleoBond® nucleic acid isolation/purification kits by Clontech Laboratories, Inc. (Mountain View, CA), and TRIzol™ reagent by Invitrogen™. In certain aspects, the RNA is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md), the RecoverAll® Total Nucleic Acid Isolation kit for FFPE by Life Technologies, Inc. (Carlsbad, CA), and the NucleoSpin® FFPE kits by Clontech Laboratories, Inc. (Mountain View, CA).

The nature of the 5' cap of the adapted RNA will vary depending on type of RNA being analyzed. In some embodiments, the RNA is prokaryotic RNA. When the RNA is prokaryotic RNA, non-limiting examples of 5' caps which may be present in the adapted RNA include 5'-adenylylation (also known as 5'-AMPylation, where AMP is adenosine monophosphate), 5' NADylation (where NAD is nicotinamide adenine dinucleotide), and a 5' triphosphate cap. A subset of RNAs of *E. coli* and *Streptomyces venezuelae*, for example, bear NAD+ at the 5' end. See, e.g., Cahová et al. (2015) Nature 519(7543):374-7. In certain aspects, the adapted RNA is an adapted prokaryotic RNA and the 5' cap present in the adapted prokaryotic RNA is a cap or cap-like structure described in Julius & Yuzenkova (2017) *Nucleic Acids Research* 45(14):8282-8290. In some embodiments, the adapted RNA is an adapted prokaryotic RNA and the 5' cap present in the adapted prokaryotic RNA is an adenine-containing cofactor. Adenine-containing cofactors of interest include, but are not limited to, NAD+, NADH, NADP+, and FAD.

In certain aspects, the RNA is a eukaryotic RNA. In some embodiments, the eukaryotic RNA is eukaryotic mRNA or eukaryotic long non-coding RNA (lncRNA). When the RNA is a eukaryotic RNA, the RNA may have a 5' cap that comprises guanosine. By "5' cap that comprises guanosine" is meant a cap that includes guanosine, derivatives thereof, and analogs thereof. In certain aspects, such a 5' cap is 7-methylguanosine (m7G). In some embodiments, such a 5' cap is a m7G analog which is demethylated at position 7. The methods may further include demethylating a m7G 5' cap to produce the guanosine analog. In certain aspects, the methods include removing the native cap of the capped RNA and replacing the native cap with a non-native cap to which the adapter polynucleotide is attached or will be attached. Details regarding eukaryotic caps may be found, e.g., in Ramanathan et al. (2016) *Nucleic Acids Research* 44(16):7511-7526.

Figure 2:
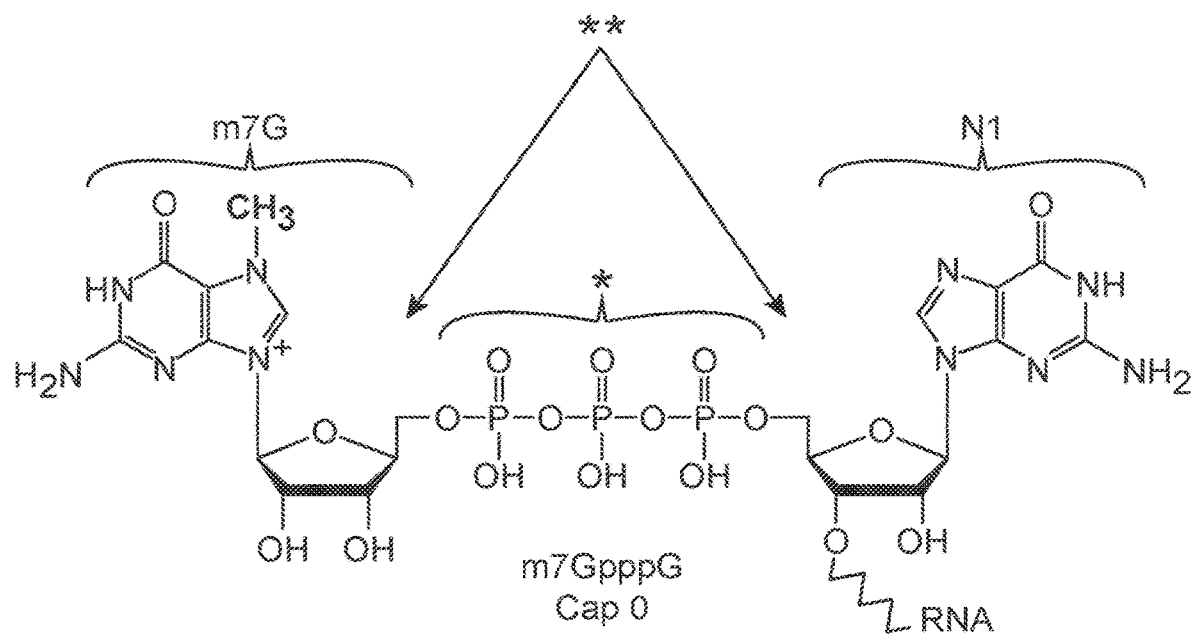
FIG. 2 The structures of eukaryotic cap 0 (top) and cap 1 (bottom). In both structures, a 7-methylguanosine (m7G) is connected to nucleotide N1 via an unusual 5' to 5' triphosphate linkage. In the cap 0 structure, the triphosphate linkage is indicated by an asterisk (*) while the 5' to 5' orientation is indicated by double asterisks (**).
Figure 2:
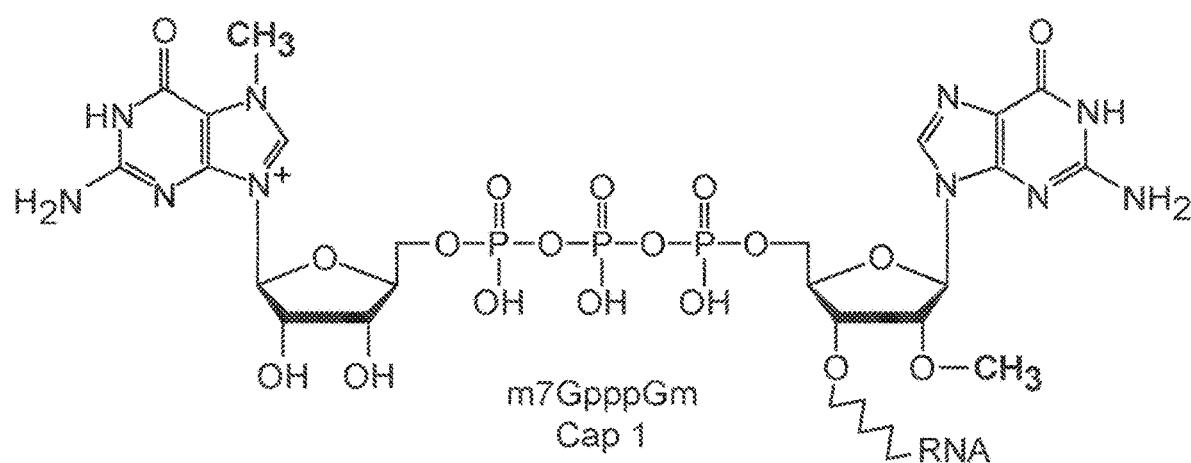

Shown in FIG. 2 are the structures of eukaryotic cap 0 (top) and cap 1 (bottom). In both structures, a 7-methylguanosine (m7G) is connected to nucleotide N1 via an unusual 5' to 5' triphosphate linkage. In the cap 0 structure, the triphosphate linkage is indicated by an asterisk (*) while the 5' to 5' orientation is indicated by double asterisks (**). As summarized above, the present methods include identifying one or more ionic current features characteristic of the 5' cap translocating through the nanopore. In certain aspects, the adapted RNA includes a triphosphate linkage between the 5' cap and nucleotide N1 of the RNA region, and the identifying includes identifying an ionic current feature characteristic of the triphosphate linkage. In some embodiments, the 5' cap and nucleotide N1 of the RNA region are in a 5' to 5' orientation, and the identifying includes identifying an ionic current feature characteristic of the 5' to 5' orientation of the 5' cap and nucleotide N1.

Cap 0 and cap 1 differ from each other in that nucleotide N1 includes a ribose 2'-O methyl group in cap 1 whereas such a modification is absent in cap 0 (FIG. 2). Cap 1 may further include a methyl group at position N7 of the base portion of nucleotide N1. Cap 2 (not shown) includes a ribose 2'-O methyl group at nucleotides N1 and N2.

In certain aspects, the present methods further include identifying an ionic current feature characteristic of a modification of one or more of nucleotides N1 to N20 translocating through the nanopore. By "N1" is meant the terminal 5' nucleotide of the RNA region of the adapted RNA—that is, the nucleotide linked directly to the 5' cap in a 5' to 5' orientation via the triphosphate linkage. Nucleotide N2 is the nucleotide bound to the 3' position of nucleotide N1, nucleotide N3 is the nucleotide bound to the 3' position of nucleotide N2, and so forth. In some embodiments, the present methods further include identifying an ionic current feature characteristic of a modification of nucleotide N1, nucleotide N2, or both. The modification may include a ribose modification. A non-limiting example of a ribose modification is a ribose 2'-O methyl group. Alternatively, or additionally, the modification may include a base modification. A non-limiting example of a base modification is methylation at position N6. In certain aspects, the methods include identifying a nucleotide in the RNA region that includes both a ribose 2'-O methyl group and methylation at position N6, a non-limiting example of which is N6,2'-O-dimethyladenosine.

As used herein, the "adapter polynucleotide" is a single-stranded multimer of nucleotides attached to the 5' cap. Attachment of the adapter polynucleotide to the 5' cap may be direct or indirect (e.g., through a linker, such as a polyethylene glycol (PEG) or other suitable linker). The adapter polynucleotide may include one or more ribonucleotide monomers. When the adapter polynucleotide includes one or more ribonucleotide monomers, the methods may include identifying one or more of the one or more ribonucleotides. The adapter polynucleotide may include one or more deoxyribonucleotide monomers. When the adapter polynucleotide includes one or more deoxyribonucleotide monomers, the methods may include identifying one or more of the one or more deoxyribonucleotides.

In some embodiments, the adapter polynucleotide includes a homopolymeric region. By "homopolymeric region" is meant a region of 5 or more consecutive identical nucleotides. In certain aspects, the homopolymeric region is a region of 10 or more, 15 or more, 20 or more, 25 or more, 30 or more, 40 or more, or 50 or more consecutive identical nucleotides. The nucleotides of the homopolymeric region may be canonical or non-canonical nucleotides. In certain aspects, the adapter polynucleotide includes a homopolymer region of inosine. Inosine is formed when hypoxanthine is attached to a ribose ring via a 13-N9-glycosidic bond. In certain aspects, when the adapter polynucleotide includes a homopolymer region of inosine, the adapter polynucleotide further includes a DNA region. When the adapter polynucleotide includes a homopolymeric region, the methods may further include identifying at least a portion of the homopolymeric region based on the ionic current through the nanopore during translocation of the homopolymeric region through the nanopore.

In certain aspects, the adapter polynucleotide includes one or more non-natural nucleotides. When the adapter polynucleotide includes one or more non-natural nucleotides, the methods may further include identifying one or more of the one or more non-natural nucleotides based on the ionic current through the nanopore during translocation of the one or more non-natural nucleotides through the nanopore. Non-limiting examples of non-natural nucleotides which may be present in the adapter polynucleotide include LNA (locked nucleic acid), PNA (peptide nucleic acid), FANA (2'-deoxy-2'-fluoroarabinonucleotide), GNA (glycol nucleic acid), TNA (threose nucleic acid), 2'-O-Me RNA, 2'-fluoro RNA, Morpholino nucleotides, and any combination thereof.

In some embodiments, the adapter polynucleotide includes one or more labels. Labels of interest include, e.g., detectable labels. As used herein, a "detectable label" is a chemical moiety that affords detectability to a molecule (e.g., polynucleotide) attached thereto. Exemplary detectable labels include fluorescent labels, luminescent labels, radioactive labels, spectroscopic labels, chelated metal labels, and the like.

In some embodiments, the adapter polynucleotide includes one or more affinity tags. The term "affinity tag," as used herein, refers to a chemical moiety that functions as, or contains, an affinity ligand that is capable of binding (e.g., non-covalently or covalently) to a second, "capture" chemical moiety, such that the nucleic acid complex or derivative thereof can be selected (or "captured") from a mixture using the capture moiety. In some embodiments, the capture moiety is bound to a solid support, e.g., a bead (e.g., a magnetic bead), planar surface, or the like. Non-limiting examples of affinity tags that may be included in the adapter polynucleotide include biotin, desthiobiotin, avidin, streptavidin, an aptamer (see, e.g., Wilson & Szostak (1999) *Annu Rev Biochem*. 68:611-647), an MS2 coat protein-interacting sequence, a U1A protein-interacting sequence, etc. Nucleic acid affinity tags that find use in the adapter polynucleotides of the present disclosure are described, e.g., in Walker et al. (2008) *Methods Mol Biol*. 488:23-40. Interactions between the affinity tag and the capture moiety may be specific and reversible (e.g., non-covalent binding or hydrolyzable covalent linkage), but if desired, may be (or subsequently may be made) irreversible, e.g., a non-hydrolyzable covalent linkage between the affinity tag and the capture moiety.

The adapter polynucleotide may be any suitable length. The length of the adapter polynucleotide may vary depending on the presence of one or more homopolymeric regions, the distance between a polynucleotide binding region of a motor protein and the detection region of the nanopore (where the length of the adapter polynucleotide is designed to be at least long enough such that the rate of translocation may be controlled by the motor protein when the cap traverses the detection region of the nanopore), and/or the like. In some embodiments, the adapter polynucleotide is from 5 to 500 nucleotides in length (e.g., 5 to 100 nucleotides in length), e.g. from 10 to 250 nucleotides, 10 to 200 nucleotides, 10 to 150 nucleotides, 10 to 100 nucleotides, 10 to 75 nucleotides, or from 10 to 50 nucleotides in length.

The manner in which the adapter polynucleotide is attached to the 5' cap may vary depending upon the type of 5' cap present in the capped RNA. In some embodiments, the capped RNA includes a 5' cap that comprises guanosine or a derivative thereof (e.g., 7-methylguanosine) and the adapter polynucleotide is attached at the 2' or 3' position of the guanosine. For example, the adapter polynucleotide may be attached at the 3' position of the guanosine. In certain aspects, the methods further include adding the adapter polynucleotide to the guanosine by polymerase-mediated extension from the attachment position of the guanosine. For example, a polymerase engineered to polymerize a polynucleotide from the 2' or 3' position of the guanosine may be employed to add the adapter polynucleotide to the 5' cap. Alternatively, the methods may further include adding the adapter polynucleotide to the guanosine by enzyme-mediated ligation to the attachment position of the guanosine. The ligation may be carried out using a suitable ligase. In some embodiments, the ligase is selected from RNA Ligase 2 (RNL2), T4 DNA Ligase, and T4 RNA Ligase 1.

In certain aspects, translocation of the adapted RNA in the 3' to 5' direction through the nanopore from the cis compartment to the trans compartment is achieved by application of a potential difference across the thin film. For example, the nanopore device may include a power source electrically coupled to electrodes, where the power source and electrodes are configured to apply a potential difference across the thin film. The potential difference results in ionic current flow and translocation of the adapted RNA from the cis compartment to the trans compartment. As used herein, translocation of the adapted RNA "from the cis compartment to the trans compartment" means that the adapted RNA is translocated in the 3' to 5' direction at least to the extent that the 5' cap is translocated passed the detection region of the nanopore. It is not required that the entire adapted RNA, including the entire adapter polynucleotide, be translocated to the trans side of the thin film. In some embodiments, the adapter includes a moiety that prevents the entire adapter from traversing the nanopore, the potential difference is reversed before the entire adapter traverses the nanopore, or both.

In some embodiments, the methods of the present disclosure further include sequencing at least a portion of the RNA region based on changes in the ionic current through the nanopore during the translocating. The sequencing may include sequencing the 5' end of the RNA region. By "sequencing the 5' end of the RNA region" is meant the identities of the nucleotides at the 5' end of the RNA region are determined, including the identity of nucleotide N1. In certain aspects, the subject methods further include sequencing at least a portion of the adapter polynucleotide—that is, determining (e.g., confirming) the identity of one or more nucleotides of the adapter polynucleotide.

Any nanopore device suitable for translocating the adapted RNA through a nanopore and monitoring ionic current through the nanopore may be employed when practicing the subject methods. For example, a suitable device may include a chamber including an aqueous solution and a thin film that separates the chamber into two sections, the membrane including a nanopore formed therein. Electrical measurements may be made using single channel recording equipment such as that described, e.g., in Lieberman et al. (2010) *J. Am. Chem. Soc.* 132(50):17961-72; Stoddart et al. (2009) PNAS 106(19):7702-7; U.S. Pat. No. 9,481,908; and U.S. Patent Application Publication No. US2014/0051068; the disclosures of which are incorporated herein by reference in their entireties for all purposes. Alternatively, electrical measurements may be made using a multi-channel system, for example as described in U.S. Patent Application Publication No. US2015346149, the disclosure of which is incorporated herein by reference in its entirety for all purposes.

In nanopore-based analysis (e.g., sequencing), the nanopore serves as a biosensor and provides the sole passage through which an ionic solution on the cis side of the membrane contacts the ionic solution on the trans side. A constant voltage bias (trans side positive) produces an ionic current through the nanopore and drives ssDNA or ssRNA in the cis chamber through the pore to the trans chamber. A processive enzyme (e.g., a helicase, polymerase, nuclease, or the like) may be bound to the polynucleotide such that its step-wise movement controls and ratchets the nucleotides through the small-diameter nanopore, nucleobase by nucleobase. Because the ionic conductivity through the nanopore is sensitive to the presence of the nucleobase's mass and its associated electrical field, the ionic current levels through the nanopore reveal the sequence of nucleobases in the translocating strand. A patch clamp, a voltage clamp, or the like, may be employed.

Suitable conditions for measuring ionic currents through transmembrane pores (e.g., protein pores, solid state pores, etc.) are known in the art. Typically, a voltage is applied across the membrane and pore. The voltage used may be from +2 V to −2 V, e.g., from −400 mV to +400 mV. The voltage used may be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage may be in the range of from 100 mV to 240 mV, e.g., from 120 mV to 220 mV.

The methods are typically carried out in the presence of a suitable charge carrier, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or I-ethyl-3-methyl imidazolium chloride. Generally, the salt is present in the aqueous solution in the chamber. Potassium chloride (KCl), sodium chloride (NaCl) or cesium chloride (CsCl) may be used, for example. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M, or from 1 M to 1.4 M. The salt concentration may be from 150 mM to 1 M. The methods are preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

In some embodiments, the rate of translocation is controlled using a processive enzyme (also referred to herein as a "motor protein"). Non-limiting examples of processive enzymes that may be employed include polymerases (e.g., a phi29 polymerase, a reverse transcriptase, or other suitable polymerase) and helicases, e.g., a He1308 helicase, a RecD helicase, a Tral helicase, a Tral subgroup helicase, an XPD helicase, or the like. The adapted RNA may be bound by the processive enzyme (e.g., by binding of the processive enzyme to a recognition site present in a sequencing adapter located at the 3' end of the adapted RNA), followed by the resulting complex being drawn to the nanopore, e.g., by a potential difference applied across the nanopore. In other aspects, the processive enzyme may be located at the nanopore (e.g., attached to or adjacent to the nanopore) such that the processive enzyme binds the 3' end of the adapted RNA upon arrival of the adapted RNA at the nanopore.

The thin film may be a solid-state film, a biological membrane, or the like. In some embodiments, the nanopore is a solid-state nanopore. In other embodiments, the nanopore is a biological nanopore. The biological nanopore may be, e.g., an alpha-hemolysin-based nanopore, a *Mycobacterium smegmatis* porin A (MspA)-based nanopore, or the like.

Nanopore devices and methods that may be employed when practicing the methods of the present disclosure include those described in U.S. Patent Application Publication Nos. US2018/0087101, US2018/0037874, US2018/0030530, US2017/0363577, US2017/0335384, US2017/0326550, US2017/0283470, US2017/0253923, US2017/0253910, US2017/0204457, US2017/0107569, US2017/0067101, US2017/0058338, US2017/0091427, US2017/0022557, US2017/0002406, US2016/0251710, US2016/0010147, US2015/0344944, US2015/0268256, and US2015/0197796, the disclosures of which are herein incorporated by reference in their entireties for all purposes.

Details regarding nanopore-based polynucleotide sequencing are described, e.g., in Feng et al. (2015) *Genomics, Proteomics & Bioinformatics* 13(1):4-16. In some embodiments, the methods of the present disclosure employ a MinION™, GridIONx5™, PromethION™, or Smidg-ION™ nanopore device, available from Oxford Nanopore Technologies. Detailed design considerations and protocols for carrying out nanopore-based analysis and sequencing are provided with such systems.

Computer-Readable Media, Computer Devices and Systems

As summarized above, the present disclosure also provides non-transitory computer readable media. Such media include instructions for analyzing the 5' end of an adapted RNA using a nanopore, where the adapted RNA includes an RNA region, a 5' cap, and an adapter polynucleotide attached to the 5' cap. When executed by a computing device, the instructions cause the computing device to monitor ionic current through a nanopore during translocation of the adapted RNA through the nanopore, and identify one or more ionic current features characteristic of the 5' cap translocating through the nanopore. In some embodiments, the adapted RNA includes a triphosphate linkage between the 5' cap and nucleotide N1 of the RNA region, and the instructions cause the computing device to identify an ionic current feature characteristic of the triphosphate linkage. In certain aspects, the 5' cap and nucleotide N1 of the RNA region are in a 5' to 5' orientation, and the instructions cause the computing device to identify an ionic current feature characteristic of the 5' to 5' orientation of the 5' cap and nucleotide N1.

The instructions of the non-transitory computer readable media of the present disclosure may further cause the computing device to identify an ionic current feature characteristic of a modification of one or more of nucleotides N1 to N20 translocating through the nanopore. For example, the instructions further cause the computing device to identify an ionic current feature characteristic of a modification of nucleotide N1, nucleotide N2, or both. The modification may include a ribose modification. A non-limiting example of a ribose modification is a ribose 2'-O methyl group. Alternatively, or additionally, the modification may include a base modification. A non-limiting example of a base modification is methylation at position N6. In certain aspects, the modification includes both a ribose 2'-O methyl group and methylation at position N6. N6,2'-O-dimethyladenosine is a nucleotide including such a modification.

The instructions of the non-transitory computer readable media of the present disclosure may further cause the computing device to sequence at least a portion of the RNA region based on changes in the ionic current through the nanopore during the translocating. In certain aspects, such instructions cause the computing device to sequence the 5' end of the RNA region—including determining the identity of nucleotide N1 as described in the Methods section herein. In some embodiments, such instructions cause the computing device to sequence at least a portion of the adapter polynucleotide.

Instructions can be coded onto a non-transitory computer-readable medium in the form of "programming," where the term "computer-readable medium" as used herein refers to any non-transitory storage or transmission medium that participates in providing instructions and/or data to a computer for execution and/or processing. Examples of storage media include a hard disk, optical disk, magneto-optical disk, CD-ROM, CD-R, magnetic tape, non-volatile memory card, ROM, DVD-ROM, Blue-ray disk, solid state disk, network attached storage (NAS), etc., whether or not such devices are internal or external to the computer. A file containing information can be "stored" on computer readable medium, where "storing" means recording information such that it is accessible and retrievable at a later date by a computer.

The instructions may be in the form of programming that is written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as many others.

Also provided by the present disclosure are computer devices. The computer devices include a processor and any of the non-transitory computer-readable media of the present disclosure. The computing device may be part of a system that includes a nanopore device, such as a MinION™, GridIONx5™, PromethION™, or SmidgION™ nanopore device, available from Oxford Nanopore Technologies.

Oxford Nanopore Technologies (ONT) sequencing adapter, a polyA tail, a synthetic GLuc mRNA, a guanosine cap, and an adapter covalently attached to the guanosine cap. The adapter includes a first PEG linker attached to the cap, a 33mer or 45mer of RNA nucleotides, a second PEG linker, and desthiobiotin at the 5' end of the PEG linker.

Figure 4:
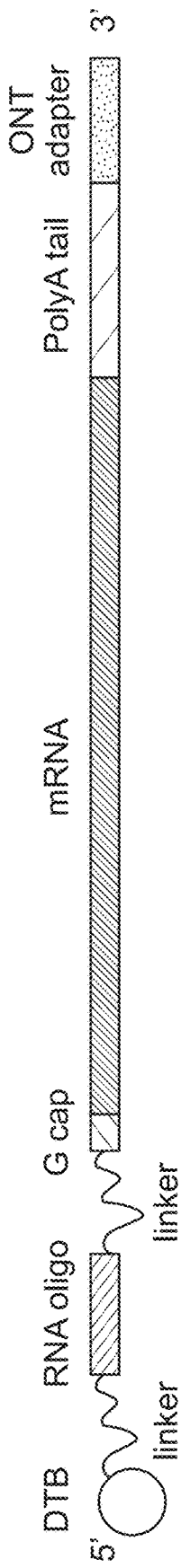
FIG. 4 A schematic illustration of an adapted RNA construct according to one embodiment. From 3' to 5', the construct includes an Oxford Nanopore Technologies (ONT) sequencing adapter, a polyA tail, a synthetic *Gaussia princeps* luciferase (Gluc) mRNA, a guanosine cap, and an adapter covalently attached to the guanosine cap. The adapter includes a first PEG linker attached to the cap, an RNA oligonucleotide (e.g., a 33mer), a second PEG linker, and desthiobiotin at the 5' end of the PEG linker.
Figure 5:
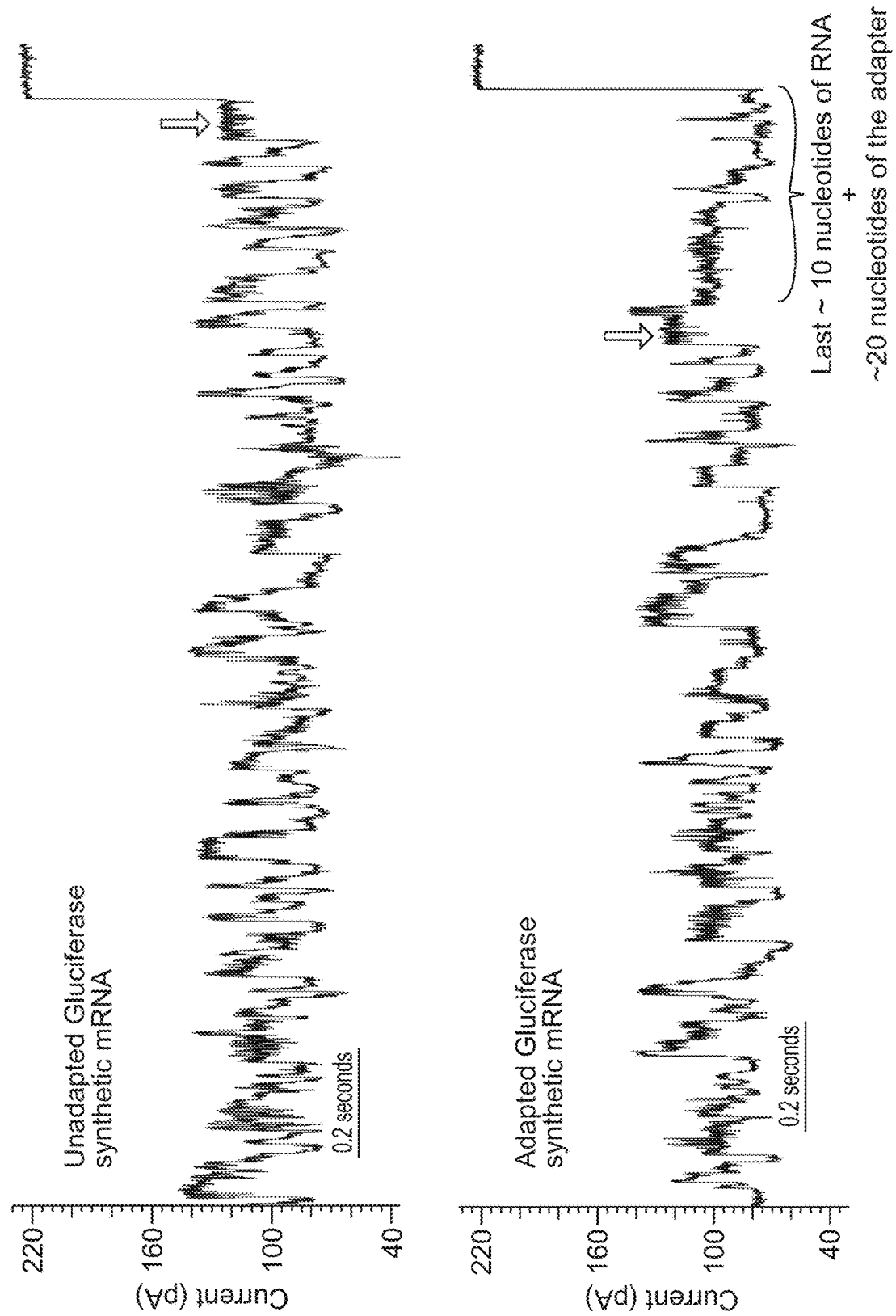
FIG. 5 Ionic current states at the 5' ends of non-adapted (top) versus adapted (bottom) GLuc mRNA molecules. Ionic current states at the 5' ends of adapted GLuc mRNA molecules that were unique to adapted molecules were observed.
Figure 6:
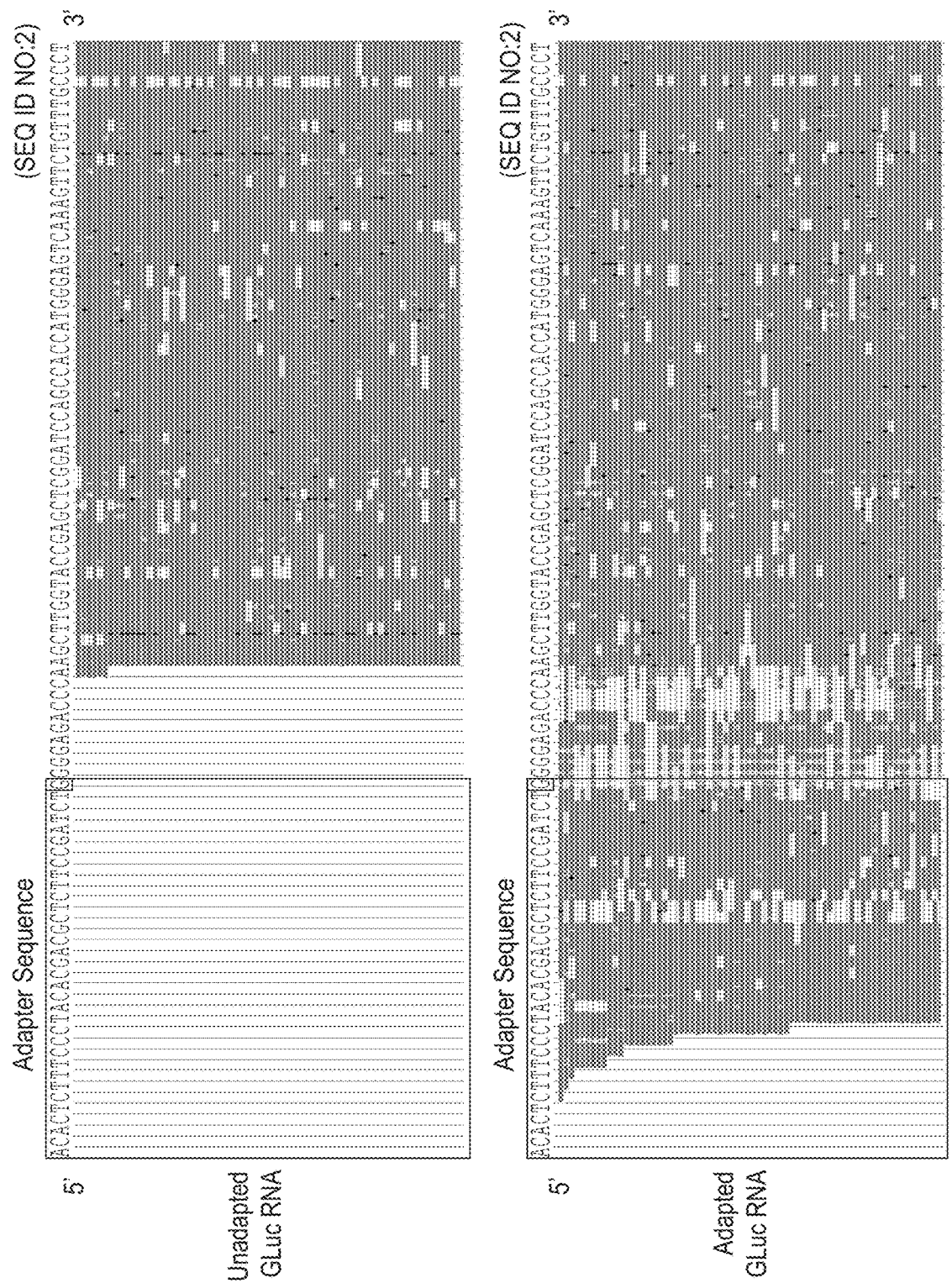
FIG. 6 Sequence alignment of non-adapted (top) and adapted (bottom) GLuc mRNA molecules to the adapted RNA sequence. When comparing multiple adapted vs. non-adapted molecules, the non-adapted molecules did not align to the adapter portion, but rather terminated ~11 nucleotides prior to the adapter.

GLuc mRNA with and without the 5' adapter shown in FIG. 4 were run on a MinION™ sequencing device. Results are shown in FIG. 5 and FIG. 6. As shown in FIG. 5, ionic current states at the 5' ends of adapted GLuc mRNA molecules that were unique to adapted molecules were observed. As shown in FIG. 6, when comparing multiple adapted vs. non-adapted molecules, the non-adapted molecules did not align to the adapter portion, but rather terminated ~11 nucleotides prior to the adapter.

Additional sequencing was performed on adapted Gluc synthetic RNA. Typical results are summarized in Table 1. For the number of pass reads, alignments, genes identified, and number of reads identified as adapted, Porechop software was used.

TABLE 1

Nanopore native RNA sequencing statistics for adapted and control synthetic mRNA transcript Gluc

| | | | pass reads | | Adapted reads | | |
|---|---|---|---|---|---|---|---|
| sample | date | experiment | reads | alignments | adapted | % of pass reads | alignments |
| Gluc | Aug. 14, 2018 | Neg control | 766085 | 737391 | 0 | 0.00% | 0 |
| Gluc | Feb. 1, 2018 | VCE propargylGTP | 61999 | 48093 | 2552 | 4.12% | 2434 |
| Gluc | Sep. 3, 2018 | TBTA 10 minutes | 516052 | 481578 | 37223 | 7.21% | 35944 |
| Gluc | Nov. 9, 2018 | 45mer adapter | 303643 | 288771 | 41014 | 13.51% | 40257 |
| Gluc | May 13, 2019 | 33mer RNA adapter CuFree click | 329390 | 317396 | 111494 | 35.13% | 110631 |

The following examples are offered by way of illustration and not by way of limitation.

EXPERIMENTAL

Introduction

Nanopore-based direct RNA sequencing reads typically terminate before reaching the end of the molecule. When a motor enzyme releases the RNA strand, the 5' nucleotides translocate too rapidly to be sequenced. Sequencing through the transcription start site (TSS), however, is important for understanding the 5' UTR, promotor positions, regulatory motifs, the true coding region, and identifying isoforms of alternatively spliced transcripts.

Figure 3:
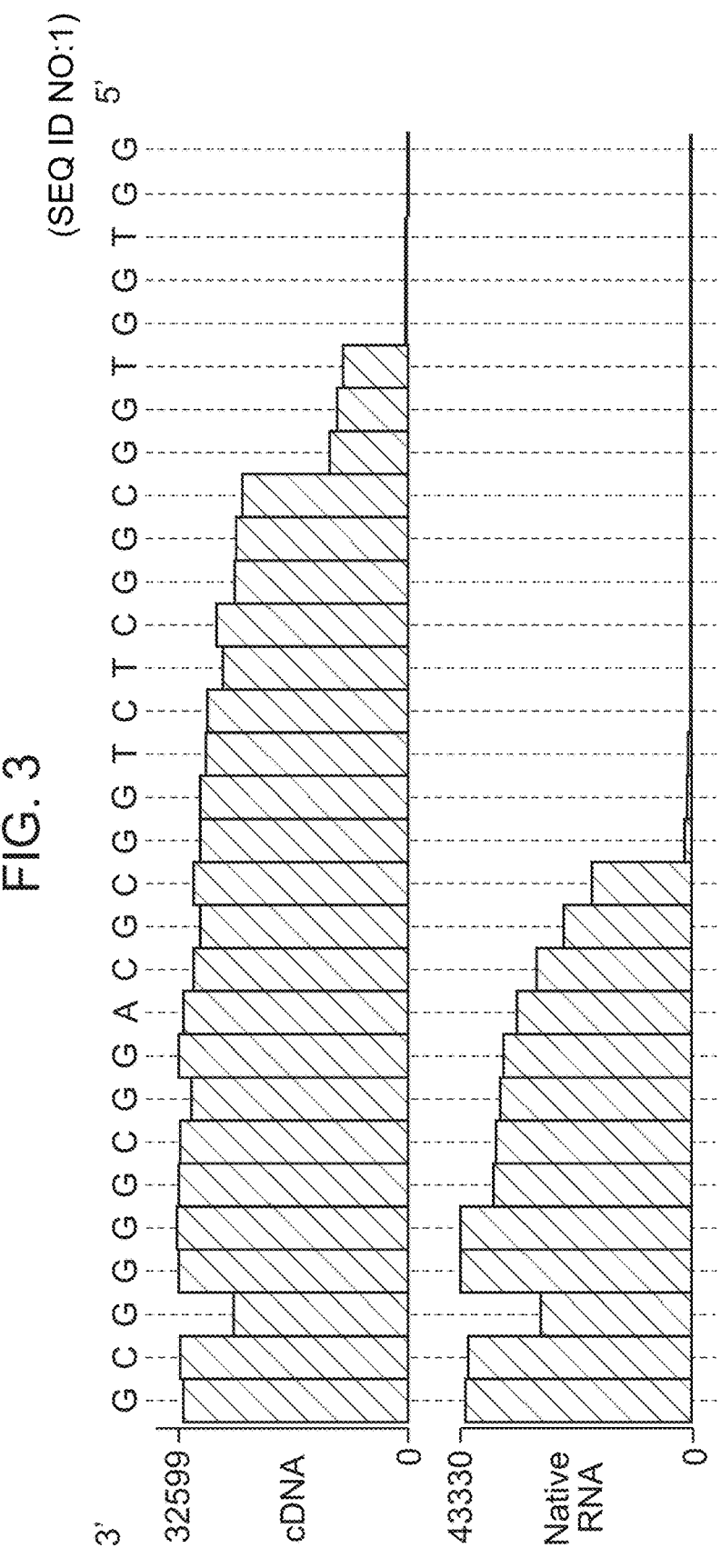
FIG. 3 Comparison of human cDNA sequencing reads to direct RNA sequencing reads, where the direct RNA reads are from non-adapted RNAs. In the non-adapted RNA sequencing reads, nucleotides are being missed due to the enzyme releasing the non-adapted RNA prior to reading of the full molecule.

When comparing human cDNA reads to Direct RNA reads, it is clear that there are RNA nucleotides being missed by the Direct RNA sequencer (FIG. 3). When sequencing cDNA, both strands are read, and additionally an adapter is added to both ends of the cDNA. Compared to the single stranded RNA with only a 3' end adapter, it becomes clear that nucleotides are being missed due to the enzyme releasing before the sensor can read the full molecule.

Example 1—Analysis of Adapted Gluc mRNA

Described herein is the addition of a marker to the 5' end of molecules to identify and sequence the true (or "biological") 5' end. In this particular example, an RNA oligonucleotide adapter was covalently attached to the 5' guanosine cap of *Gaussia princeps* luciferase (Gluciferase, or "GLuc") mRNA molecules, which enabled a MinION™ sequencing device to sequence through the true 5' end of the RNA molecules.

Figure 7:
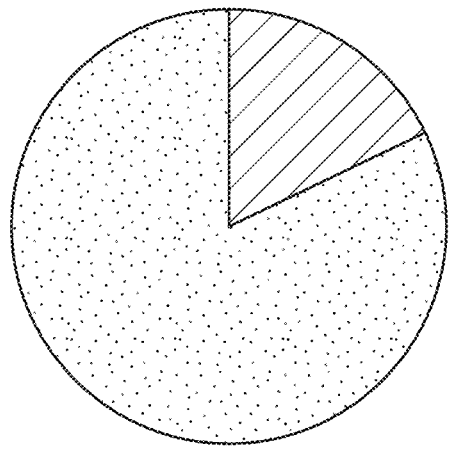
FIG. 7 Summary of sequencing results for adapted yeast YCT11 polyA RNA.
Figure 7:
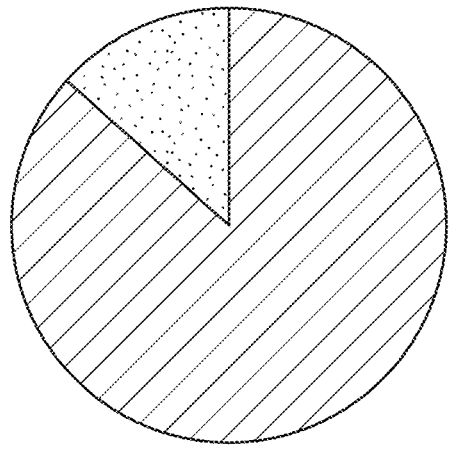

The adapted RNA construct is schematically illustrated in FIG. 4. As shown, the construct includes, from 3' to 5', an Example 2—Analysis of Adapted Yeast YCT11 polyA RNA Next, a biological eukaryotic substrate was used as the substrate. In this particular example, sequencing was performed on adapted yeast YCT11 polyA RNA. Results are summarized in FIG. 7. The smaller slice in the pie chart on the left is the proportion of all the adapted nanopore reads that contain a predicted transcription start site (TSS). The larger slice in the pie chart on the right is the proportion of reads that contain the adapter sequence and a TSS.

Example 3—Analysis of Adapted Yeast S288C polyA RNA

Figure 8:
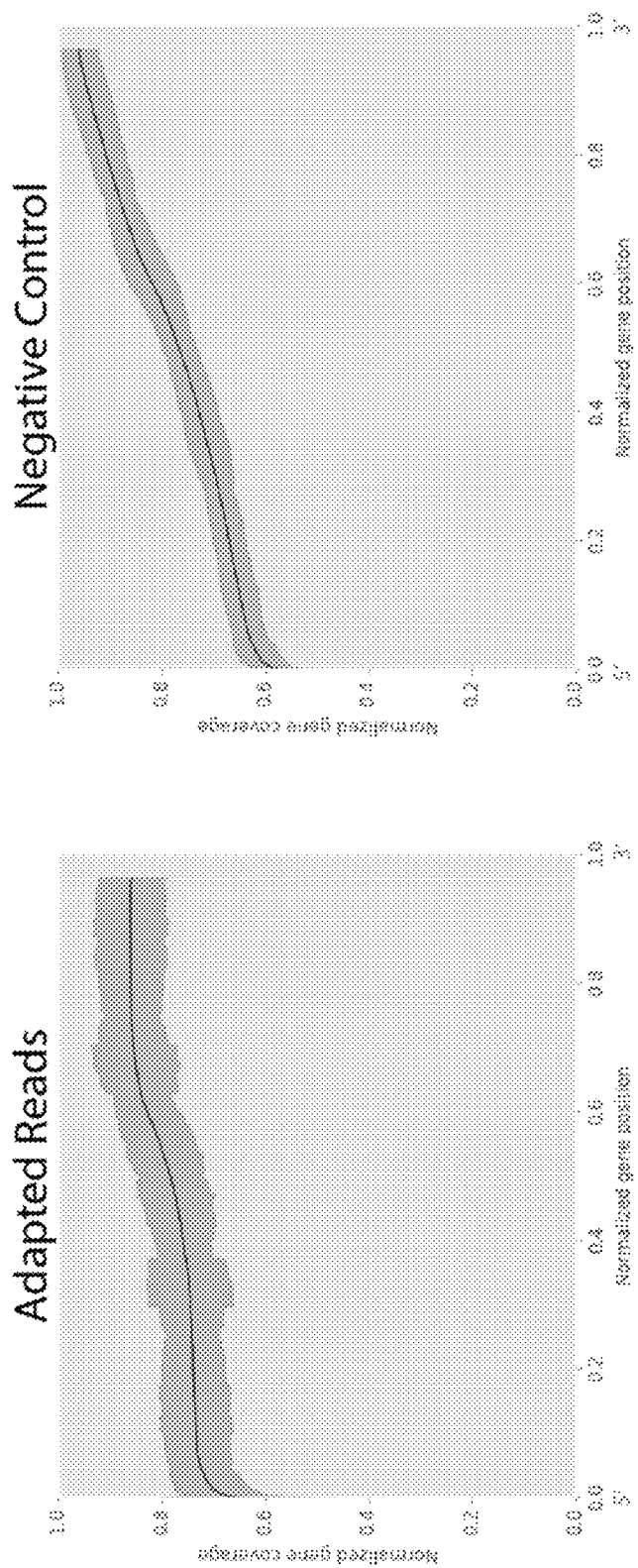
FIG. 8 Normalized coverage plots for the 45mer click adapted reads and control yeast S288C polyA RNA samples. The length for all annotated yeast genes are normalized to a 0 to 1 scale (x-axis). The normalized average coverage for each base in each gene is plotted as a line for both the negative control sample and for adapted reads. The shaded area represents two standard deviations around the mean.

A further biological eukaryotic substrate was used as the substrate. In this particular example, sequencing was performed on adapted yeast S288C polyA RNA. Shown in FIG. 8 are normalized coverage plots for the 45mer click adapted reads and control yeast S288C polyA RNA samples. The length for all annotated yeast genes are normalized to a 0 to 1 scale (x-axis). The normalized average coverage for each base in each gene is plotted as a line for both the negative control sample and for adapted reads. The shaded area represents two standard deviations around the mean.

Figure 9:
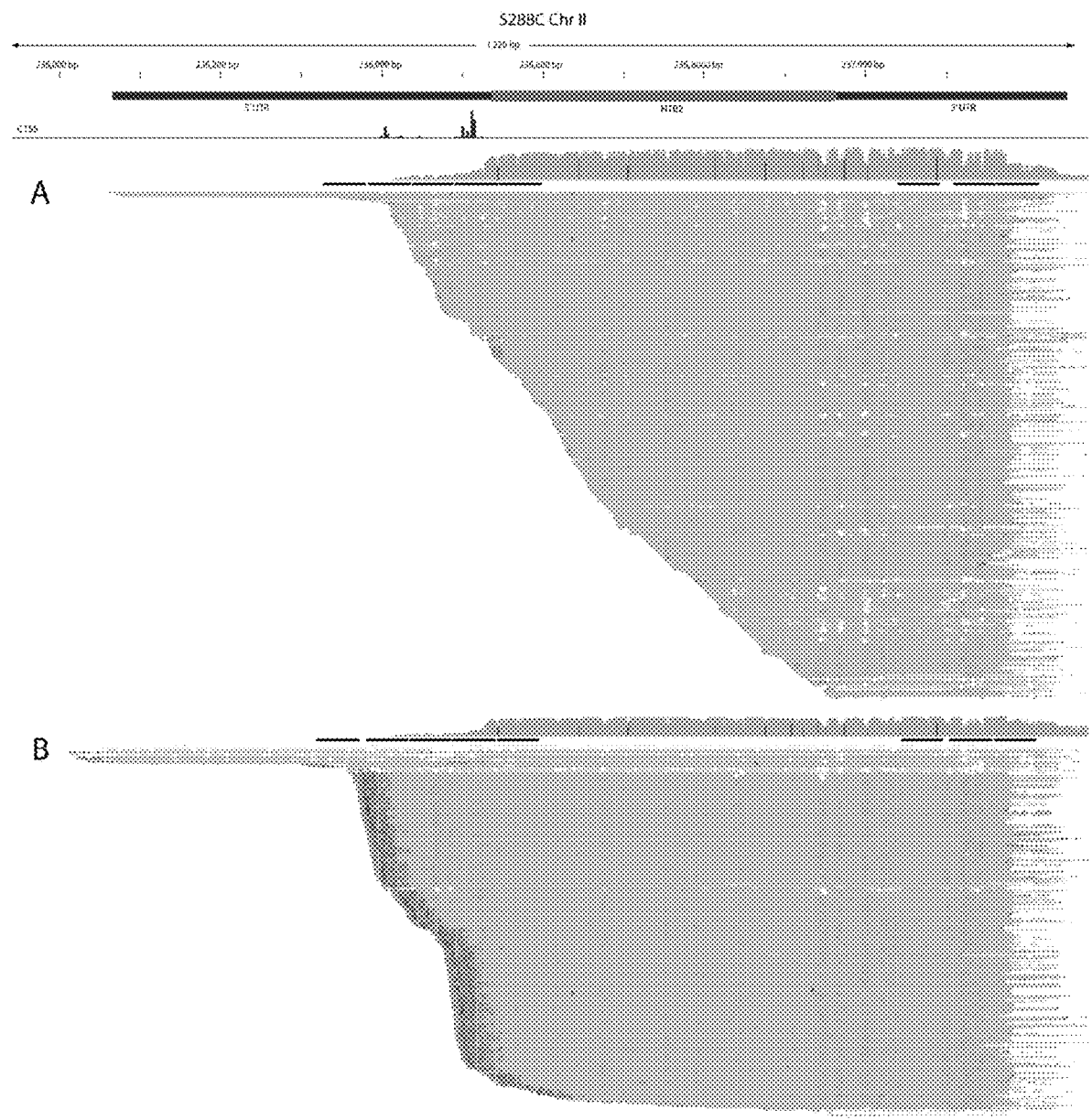
FIG. 9 Coverage and alignment plots for yeast S288C control sample (a) and the 45mer click adapted reads (b). Highlighted in red is the coding region for the gene HTB2 and the blue bars are the untranslated regions (UTRS) for the gene. There are two distinct transcription start site (TSS) regions and it is difficult to determine which one is being used in the negative control sample. The soft clipped bases in the alignment for the adapted reads (red and blue tracks on the 5' end) make it easier to determine which of the two TSSs are being used.

Shown in FIG. 9 are coverage and alignment plots for yeast S288C control sample (a) and the 45mer click adapted reads (b). Highlighted in red is the coding region for the gene HTB2 and the blue bars are the untranslated regions (UTRS) for the gene. There are two distinct transcription start site (TSS) regions and it is difficult to determine which one is being used in the negative control sample. The soft clipped bases in the alignment for the adapted reads (red and blue tracks on the 5' end) make it easier to determine which of the two TSSs are being used.

The sequencing results for yeast S288C polyA RNA are summarized in Table 2. For the number of pass reads, alignments, genes identified, and number of reads identified as adapted, Porechop software was used.

TABLE 2

Nanopore native RNA sequencing statistics for adapted and control yeast strain S288C poly(A) RNA

| | | | pass reads | | | Adapted reads | | | |
|---|---|---|---|---|---|---|---|---|---|
| sample | date | experiment | reads | alignments | genes identified | reads | % of pass reads | alignments | genes identified |
| S288C | Nov. 27, 2018 | negative control | 1317824 | 924137 | 5839 | 0 | 0.00% | 0 | 0 |
| S288C | Dec. 19, 2018 | negative control | 1717846 | 1557352 | 5938 | 0 | 0.00% | 0 | 0 |
| S288C | Feb. 7, 2019 | negative control | 3102860 | 2858286 | 5852 | 0 | 0.00% | 0 | 0 |
| S288C | Mar. 15, 2019 | 45mer technical repeat B2 | 551454 | 339319 | 5451 | 26307 | 4.77% | 21468 | 1397 |
| S288C | Mar. 13, 2019 | 45mer technical repeat A2 | 1316785 | 1026068 | 5738 | 70389 | 5.35% | 62151 | 2812 |
| S288C | Feb. 9, 2019 | 45mer technical repeat A1 | 3767770 | 3065453 | 6063 | 266984 | 7.09% | 237764 | 4381 |
| S288C | Feb. 9, 2019 | 45mer technical repeat B1 | 1795825 | 1562367 | 5764 | 210264 | 11.71% | 194113 | 4307 |
| S288C | Nov. 2, 2018 | 45mer | 2486455 | 2,088,529 | 6015 | 484,563 | 19.49% | 438220 | 5092 |

Notwithstanding the appended claims, the present disclosure is also defined by the following clauses:

1. A method of analyzing a capped ribonucleic acid (RNA) using a nanopore, comprising:
   translocating an adapted RNA through a nanopore of a nanopore device, wherein the nanopore devices comprises a thin film separating a cis compartment from a trans compartment, the thin film comprising the nanopore therein, and wherein:
   the adapted RNA is translocated in the 3' to 5' direction through the nanopore from the cis compartment to the trans compartment,
   the adapted RNA comprises an RNA region, a 5' cap, and an adapter polynucleotide attached to the 5' cap, and
   the translocating comprises translocating the 5' cap through the nanopore;
   monitoring ionic current through the nanopore during the translocating, wherein the rate of translocation is controlled to permit discrimination of individual nucleotides of the adapted RNA based on changes in the ionic current; and
   identifying one or more ionic current features characteristic of the 5' cap translocating through the nanopore.

2. The method according to Clause 1, wherein the adapted RNA comprises a triphosphate linkage between the 5' cap and nucleotide N1 of the RNA region, and wherein the identifying comprises identifying an ionic current feature characteristic of the triphosphate linkage.

3. The method according to Clause 1 or Clause 2, wherein the 5' cap and nucleotide N1 of the RNA region are in a 5' to 5' orientation, and wherein the identifying comprises identifying an ionic current feature characteristic of the 5' to 5' orientation of the 5' cap and nucleotide N1.

4. The method according to any one of Clauses 1 to 3, further comprising identifying an ionic current feature characteristic of a modification of one or more of nucleotides N1 to N20 translocating through the nanopore.

5. The method according to any one of Clauses 1 to 3, further comprising identifying an ionic current feature characteristic of a modification of nucleotide N1, nucleotide N2, or both.

6. The method according to any one of Clauses 1 to 3, further comprising identifying an ionic current feature characteristic of a modification of nucleotide N2.

7. The method according to any one of Clauses 1 to 3, further comprising identifying an ionic current feature characteristic of a modification of nucleotide N1.

8. The method according to any one of Clauses 4 to 7, wherein the modification comprises a ribose modification.

9. The method according to Clause 8, wherein the ribose modification is a ribose 2'-O methyl group.

10. The method according to any one of Clauses 4 to 9, wherein the modification comprises a base modification.

11. The method according to Clause 10, wherein the base modification is methylation at position N6.

12. The method according to any one of Clauses 9 to 11, wherein the nucleotide is N6,2'-O-dimethyladenosine.

13. The method according to any one of Clauses 1 to 12, wherein the adapter polynucleotide comprises one or more ribonucleotides.

14. The method according to Clause 13, comprising identifying one or more of the one or more ribonucleotides.

15. The method according to any one of Clauses 1 to 14, wherein the adapter polynucleotide comprises one or more deoxyribonucleotides.

16. The method according to Clause 15, comprising identifying one or more of the one or more deoxyribonucleotides.

17. The method according to any one of Clauses 1 to 16, wherein the adapter polynucleotide comprises a homopolymeric region.

18. The method according to Clause 17, wherein the homopolymeric region comprises a homopolymer of inosine.

19. The method according to Clause 18, wherein the adapter polynucleotide comprises a DNA region in addition to the homopolymer of inosine.

20. The method according to any one of Clauses 17 to 19, comprising identifying at least a portion of the homopolymeric region.

21. The method according to any one of Clauses 1 to 20, wherein the adapter polynucleotide comprises one or more non-natural nucleotides.

22. The method according to Clause 21, comprising identifying one or more of the one or more non-natural nucleotides.

23. The method according to any one of Clauses 1 to 22, wherein the adapter polynucleotide is from 5 to 100 nucleotides in length.

24. The method according to any one of Clauses 1 to 23, wherein the 5' cap comprises guanosine.

25. The method according to Clause 24, wherein the 5' cap is 7-methylguanosine.

26. The method according to Clause 24, wherein the guanosine is a guanosine analog.

27. The method according to Clause 26, wherein the guanosine analog is a demethylated derivative of a 7-methylguanosine 5' cap.

28. The method according to Clause 27, further comprising demethylating the 7-methylguanosine 5' cap to produce the guanosine analog.

29. The method according to any one of Clauses 24 to 28, wherein the adapter polynucleotide is attached at the 2' or 3' position of the guanosine.

30. The method according to Clause 29, wherein the adapter polynucleotide is attached at the 3' position of the guanosine.

31. The method according to Clause 29 or Clause 30, further comprising adding the adapter polynucleotide to the guanosine by polymerase-mediated extension from the attachment position of the guanosine.

32. The method according to Clause 29 or Clause 30, further comprising adding the adapter polynucleotide to the guanosine by enzyme-mediated ligation to the attachment position of the guanosine.

33. The method according to Clause 32, wherein the enzyme is a ligase.

34. The method according to Clause 33, wherein the ligase is selected from the group consisting of: RNA Ligase 2 (RNL2), T4 DNA Ligase, and T4 RNA Ligase 1.

35. The method according to any one of Clauses 1 to 34, wherein during the translocating, the adapted RNA is part of a complex comprising an RNA motor protein and the adapted RNA, and wherein the rate of translocation is controlled by the motor protein.

36. The method according to Clause 35, wherein the motor protein is complexed with the adapter polynucleotide during translocation of the 5' cap through the nanopore.

37. The method according to Clause 35 or Clause 36, wherein the motor protein is selected from the group consisting of: an RNA helicase, a DNA helicase, and a reverse transcriptase.

38. The method according to any one of Clauses 1 to 37, further comprising sequencing at least a portion of the RNA region based on changes in the ionic current through the nanopore during the translocating.

39. The method according to Clause 38, wherein the sequencing comprises sequencing the 5' end of the RNA region.

40. The method according to Clause 38 or Clause 39, further comprising sequencing at least a portion of the adapter polynucleotide.

41. The method according to any one of Clauses 1 to 40, wherein the RNA is messenger RNA (mRNA).

42. The method according to any one of Clauses 1 to 40, wherein the RNA is long non-coding RNA (lncRNA).

43. A non-transitory computer readable medium comprising instructions for analyzing the 5' end of an adapted RNA using a nanopore, wherein the adapted RNA comprises an RNA region, a 5' cap, and an adapter polynucleotide attached to the 5' cap, wherein the instructions, when executed by a computing device, cause the computing device to:
   monitor ionic current through a nanopore during translocation of the adapted RNA through the nanopore; and
   identify one or more ionic current features characteristic of the 5' cap translocating through the nanopore.

44. The non-transitory computer readable medium of Clause 43, wherein the adapted RNA comprises a triphosphate linkage between the 5' cap and nucleotide N1 of the RNA region, and wherein the instructions cause the computing device to identify an ionic current feature characteristic of the triphosphate linkage.

45. The non-transitory computer readable medium of Clause 43 or Clause 44, wherein the 5' cap and nucleotide N1 of the RNA region are in a 5' to 5' orientation, and wherein the instructions cause the computing device to identify an ionic current feature characteristic of the 5' to 5' orientation of the 5' cap and nucleotide N1.

46. The non-transitory computer readable medium of any one of Clauses 43 to 45, wherein the instructions further cause the computing device to identify an ionic current feature characteristic of a modification of one or more of nucleotides N1 to N20 translocating through the nanopore.

47. The non-transitory computer readable medium of any one of Clauses 43 to 45, wherein the instructions further cause the computing device to identify an ionic current feature characteristic of a modification of nucleotide N1, nucleotide N2, or both.

48. The non-transitory computer readable medium of any one of Clauses 43 to 45, wherein the instructions further cause the computing device to identify an ionic current feature characteristic of a modification of nucleotide N2.

49. The non-transitory computer readable medium of any one of Clauses 43 to 45, wherein the instructions further cause the computing device to identify an ionic current feature characteristic of a modification of nucleotide N1.

50. The non-transitory computer readable medium of any one of Clauses 46 to 49, wherein the modification comprises a ribose modification.

51. The non-transitory computer readable medium of Clause 50, wherein the ribose modification is a ribose 2'-O methyl group.

52. The non-transitory computer readable medium of any one of Clauses 46 to 51, wherein the modification comprises a base modification.

53. The non-transitory computer readable medium of Clause 52, wherein the base modification is methylation at position N6.

54. The non-transitory computer readable medium of any one of Clauses 50 to 53, wherein the nucleotide is N6,2'-O-dimethyladenosine.

55. The non-transitory computer readable medium of any one of Clauses 43 to 54, wherein the instructions further cause the computing device to sequence at least a portion of the RNA region based on changes in the ionic current through the nanopore during the translocating.

56. The non-transitory computer readable medium of Clause 55, wherein the instructions cause the computing device to sequence the 5' end of the RNA region.

57. The non-transitory computer readable medium of any one of Clauses 43 to 56, wherein the instructions further cause the computing device to sequence at least a portion of the adapter polynucleotide.

58. A computing device, comprising:
   a processor; and
   the non-transitory computer readable medium of any one of Clauses 43 to 57.

59. The computing device of Clause 58, wherein the computing device is part of a system comprising a nanopore sequencing device.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

identifying an ionic current feature characteristic of a modification of one or more of nucleotides N1 to N20 of the RNA region translocating through the nanopore.

2. The method according to claim 1, further comprising identifying an ionic current feature characteristic of a modification of nucleotide N1, nucleotide N2, or both.

3. The method according to claim 2, wherein the modification comprises a ribose modification.

4. The method according to claim 3, wherein the ribose modification is a ribose 2'-O methyl group.

5. The method according to claim 4, wherein nucleotide N1, nucleotide N2, or both are N6,2'-O-dimethyladenosine.

6. The method according to claim 1, wherein the modification comprises a base modification.

7. The method according to claim 6, wherein the base modification is methylation at position N6.

What is claimed is:

1. A method of analyzing a capped ribonucleic acid (RNA) using a nanopore, comprising:
   translocating a capped RNA through a nanopore of a nanopore device, wherein the nanopore device comprises a membrane separating a cis compartment from a trans compartment, the membrane comprising the nanopore therein, wherein the capped RNA comprises an RNA region comprising nucleotides N1 to N20, a 5' cap, and an adapter polynucleotide attached to the 5' cap, where the 5' cap and nucleotide N1 of the RNA region are in a 5' to 5' orientation and wherein:
      the capped RNA is translocated in the 3' to 5' direction with respect to the RNA region through the nanopore from the cis compartment to the trans compartment, and
      the translocating comprises translocating the 5' cap through the nanopore;
   monitoring ionic current through the nanopore during the translocating, wherein the rate of translocation is controlled to permit discrimination of individual nucleotides of the capped RNA based on changes in the ionic current; and 8. The method according to claim 1, wherein the adapter polynucleotide comprises one or more ribonucleotides, the method further comprising identifying the one or more ribonucleotides.

9. The method according to claim 1, wherein the adapter polynucleotide comprises one or more deoxyribonucleotides, the method further comprising identifying the one or more deoxyribonucleotides.

10. The method according to claim 1, wherein the adapter polynucleotide comprises a homopolymeric region, the method further comprising identifying at least a portion of the homopolymeric region.

11. The method according to claim 10, wherein the homopolymeric region comprises a homopolymer of inosine.

12. The method according to claim 11, wherein the adapter polynucleotide further comprises a DNA region.

13. The method according to claim 1, wherein the adapter polynucleotide comprises one or more non-natural nucleotides, the method further comprising identifying one or more of the non-natural nucleotides.

14. The method according to claim 1, wherein the adapter polynucleotide is from 5 to 100 nucleotides in length.

15. The method according claim 1, wherein the 5' cap comprises guanosine or a guanosine analog.

16. The method according to claim 15, wherein the 5' cap comprises 7-methylguanosine.

17. The method according to claim 15, wherein the guanosine analog is a demethylated derivative of a 7-methylguanosine 5' cap.

18. The method according to claim 17, further comprising demethylating the 7-methylguanosine 5' cap to produce the guanosine analog.

19. The method according to claim 15, wherein the adapter polynucleotide is attached at the 2' or 3' position of the guanosine or guanosine analog.

20. The method according to claim 19, further comprising adding the adapter polynucleotide to the guanosine or guanosine analog by polymerase-mediated extension from the attachment position of the guanosine or guanosine analog.

21. The method according to claim 19, further comprising adding the adapter polynucleotide to the guanosine or guanosine analog by enzyme-mediated ligation to the attachment position of the guanosine, where the enzyme-mediated ligation is performed using a ligase.

22. The method according to claim 21, wherein the ligase is selected from the group consisting of: RNA Ligase 2 (RNL2), T4 DNA Ligase, and T4 RNA Ligase 1.

23. The method according to claim 1, further comprising sequencing at least a portion of the RNA region based on changes in the ionic current through the nanopore during the translocating.

24. The method according to claim 23, wherein the sequencing comprises sequencing the 5' end of the RNA region.

25. The method according to claim 23, further comprising sequencing at least a portion of the adapter polynucleotide.

* * * * *

UNITED STATES PATENT AND TRADEMARK OFFICE
CERTIFICATE OF CORRECTION

| | | |
|---|---|---|
| PATENT NO. | : 12,195,794 B2 | Page 1 of 1 |
| APPLICATION NO. | : 17/056378 | |
| DATED | : January 14, 2025 | |
| INVENTOR(S) | : Logan Mulroney et al. | |

It is certified that error appears in the above-identified patent and that said Letters Patent is hereby corrected as shown below:

In the Specification

In Column 2, Line 6, delete "Il-" and insert -- II- --.

In Column 5, Line 43, delete "promotor" and insert -- promoter --.

In Column 7, Line 7, delete "venezue/ae," and insert -- venezuelae, --.

In Column 8, Line 38, delete "13-" and insert -- β- --.

In Column 11, Line 11, delete "I-" and insert -- 1- --.

In Column 11, Line 33, delete "He1308" and insert -- Hel308 --.

In Column 13, Line 44, delete "promotor" and insert -- promoter --.

In the Claims

In Column 21, Line 1, in Claim 15, after "according" insert -- to --.

Signed and Sealed this
Sixth Day of May, 2025

Coke Morgan Stewart
*Acting Director of the United States Patent and Trademark Office*